(12) United States Patent
Collins et al.

(10) Patent No.: US 11,278,414 B2
(45) Date of Patent: Mar. 22, 2022

(54) CERAMIC FEMORAL RESURFACING HEAD PROSTHESIS

(71) Applicant: MatOrtho Limited, Surrey (GB)

(72) Inventors: Simon Collins, Tetbury (GB); Andrew Clive Taylor, Chichester (GB); Michael Antony Tuke, Surrey (GB); Carolina Avila Carrasco, Surrey (GB)

(73) Assignee: MatOrtho Limited, Surrey (GB)

( * ) Notice: Subject to any disclaimer, the term of this patent is extended or adjusted under 35 U.S.C. 154(b) by 0 days.

(21) Appl. No.: 16/759,406

(22) PCT Filed: Nov. 1, 2018

(86) PCT No.: PCT/GB2018/053182
§ 371 (c)(1),
(2) Date: Apr. 27, 2020

(87) PCT Pub. No.: WO2019/086889
PCT Pub. Date: May 9, 2019

(65) Prior Publication Data
US 2020/0323639 A1    Oct. 15, 2020

(30) Foreign Application Priority Data
Nov. 1, 2017 (GB) .................................. 1718082

(51) Int. Cl.
*A61F 2/36* (2006.01)
*A61F 2/30* (2006.01)
*A61F 2/46* (2006.01)

(52) U.S. Cl.
CPC ........ *A61F 2/3603* (2013.01); *A61F 2/30771* (2013.01); *A61F 2/3609* (2013.01);
(Continued)

(58) Field of Classification Search
CPC ........ A61F 2/3603; A61F 2/36; A61F 2/3609; A61F 2/4609; A61F 2002/30327;
(Continued)

(56) References Cited

U.S. PATENT DOCUMENTS

| 4,224,699 A | 9/1980 | Weber |
| 4,752,296 A * | 6/1988 | Buechel ................ A61F 2/40 623/23.14 |

(Continued)

FOREIGN PATENT DOCUMENTS

| DE | 2751537 | 5/1979 |
| EP | 1570816 | 3/2005 |

(Continued)

OTHER PUBLICATIONS

Search Report of GB Intellectual Property Office in related application No. GB1718082.9, Claims 48-61, dated Dec. 15, 2017, 1 page.

(Continued)

*Primary Examiner* — Alvin J Stewart
(74) *Attorney, Agent, or Firm* — Bochner IP, PLLC; Andrew D. Bochner

(57) ABSTRACT

A ceramic femoral resurfacing head prosthesis (110) comprises a ceramic convex outer contact surface (112) engagable with an acetabulum of a patient or an acetabular cup prosthesis and a concave inner fixation surface (114) having an inner-land portion (128), the ceramic convex outer contact surface (112) and the concave inner fixation surface (114) extending to intersect each other at a rim (116). A ceramic stem (120) projects from the concave inner fixation surface (114), and is adapted to be received by a stem bore. The concave inner fixation surface (114) includes a skirt (134) which is cylindrical or substantially cylindrical, or frusto-conical or substantially frusto-conical, and at least (Continued)

one circumferentially elongate recess (136) at the skirt (134).

12 Claims, 9 Drawing Sheets

(52) U.S. Cl.
CPC .. *A61F 2/4609* (2013.01); *A61F 2002/30327* (2013.01); *A61F 2002/30593* (2013.01); *A61F 2002/30616* (2013.01); *A61F 2002/30822* (2013.01); *A61F 2002/30881* (2013.01); *A61F 2002/3605* (2013.01); *A61F 2002/3615* (2013.01)

(58) Field of Classification Search
CPC .. A61F 2002/30616; A61F 2002/30822; A61F 2002/3605; A61F 2002/3615
See application file for complete search history.

(56) References Cited

U.S. PATENT DOCUMENTS

| | | | |
|---|---|---|---|
| 6,063,124 A | 5/2000 | Amstutz | |
| 7,255,717 B2 * | 8/2007 | Park | A61F 2/3603 623/23.12 |
| 7,338,498 B2 * | 3/2008 | Long | A61B 17/1684 606/102 |
| 7,361,194 B2 * | 4/2008 | Carroll | A61F 2/36 623/22.15 |
| 9,974,657 B2 * | 5/2018 | McMinn | A61F 2/3603 |
| 2002/0022889 A1 | 2/2002 | Chibrac | A61F 2/389 623/18.11 |
| 2006/0085079 A1 * | 4/2006 | Carroll | A61F 2/468 623/22.15 |
| 2006/0184251 A1 * | 8/2006 | Zhang | A61L 27/50 623/23.56 |
| 2007/0162149 A1 | 6/2007 | Kropf | |
| 2008/0033577 A1 * | 2/2008 | Kohan | A61F 2/3603 623/32 |
| 2009/0018666 A1 * | 1/2009 | Grundei | A61F 2/32 623/22.21 |
| 2009/0149965 A1 * | 6/2009 | Quaid | A61B 34/30 623/22.4 |
| 2009/0192620 A1 | 7/2009 | Ebbitt | |
| 2009/0248170 A1 * | 10/2009 | Tuke | A61B 17/175 623/23.11 |
| 2009/0306788 A1 * | 12/2009 | Timoteo | A61B 17/15 623/23.14 |
| 2010/0049329 A1 * | 2/2010 | Vio | A61F 2/3603 623/23.12 |
| 2010/0305713 A1 * | 12/2010 | Grundei | A61F 2/3603 623/23.12 |
| 2010/0312353 A1 | 12/2010 | Howald | |
| 2012/0029650 A1 * | 2/2012 | Bruce | A61F 2/3603 623/22.4 |
| 2013/0060347 A1 * | 3/2013 | McMinn | A61F 2/3603 623/23.23 |
| 2015/0335437 A1 | 11/2015 | Bruun Lauritzen et al. | |
| 2016/0045320 A1 | 2/2016 | Klinger et al. | |
| 2016/0113771 A1 * | 4/2016 | McMinn | A61F 2/3603 623/23.11 |
| 2018/0325695 A1 * | 11/2018 | Wozencroft | A61F 2/4607 |
| 2020/0323639 A1 * | 10/2020 | Collins | A61F 2/4603 |
| 2021/0045881 A1 * | 2/2021 | Melozzi | A61F 2/3603 |

FOREIGN PATENT DOCUMENTS

| | | |
|---|---|---|
| EP | 1900344 | 3/2008 |
| FR | 2996443 | 4/2014 |
| GB | 2396561 | 6/2004 |
| GB | 2434749 | 8/2007 |
| GB | 2531589 | 4/2016 |
| MX | 2012011866 | 4/2014 |
| WO | WO2004032987 | 4/2004 |
| WO | WO2008037978 | 4/2008 |

OTHER PUBLICATIONS

Search Report of GB Intellectual Property Office in related application No. GB1718082.9, Claims 27-34, dated Dec. 15, 2017, 1 page.
Search Report of GB Intellectual Property Office in related application No. GB1718082.9, Claims 1-26, dated Dec. 15, 2017, 1 page.
Search Report of GB Intellectual Property Office in related application No. GB1718082.9, Claims 62-75, dated Dec. 14, 2017, 2 pages.
Search Report of GB Intellectual Property Office in related application No. GB1718082.9, Claims 35-47, dated Dec. 14, 2017, 2 pages.
Search Report of GB Intellectual Property Office in related application No. GB1802167.5, dated Feb. 27, 2018, 4 pages.
Search Report of GB Intellectual Property Office in related application No. GB1906631.5, dated May 23, 2019, 2 pages.
Examination Report of GB Intellectual Property Office in related application No. GB1906631.5, dated Feb. 19, 2020, 2 pages.
International Search Report and Written Opinion in related application PCT/GB2018/053182, dated Feb. 21, 2019, 10 pages.
Examination Report of GB Intellectual Property Office in related application No. GB1912801.6, dated May 5, 2020, 4 pages.
Examination Report of GB Intellectual Property Office in related application No. GB1912801.6, dated Jan. 30, 2020, 5 pages.
Search Report of GB Intellectual Property Office in related application No. GB1912801.6, dated Jan. 29, 2020, 1 page.
Search Report of GB Intellectual Property Office in related application No. GB1905809.8, dated May 3, 2019, 1 page.
Examination Report of GB Intellectual Property Office in related application No. GB1905809.8, dated Aug. 15, 2019, 4 pages.
Examination Report of GB Intellectual Property Office in related application No. GB1905809.8, dated Oct. 2, 2019, 2 pages.
Examination Report of GB Intellectual Property Office in related application No. GB1905809.8, dated Nov. 14, 2019, 1 page.
Examination Report of GB Intellectual Property Office in related application No. GB1718082.9, dated Aug. 24, 2021, 8 pages.
Examination Report of GB Intellectual Property Office in related application No. GB1718082.9, dated Aug. 24, 2021, 2 pages.
Search Report of GB Intellectual Property Office in related application No. GB1912801.6, dated Jun. 28, 2021, 3 pages.

* cited by examiner

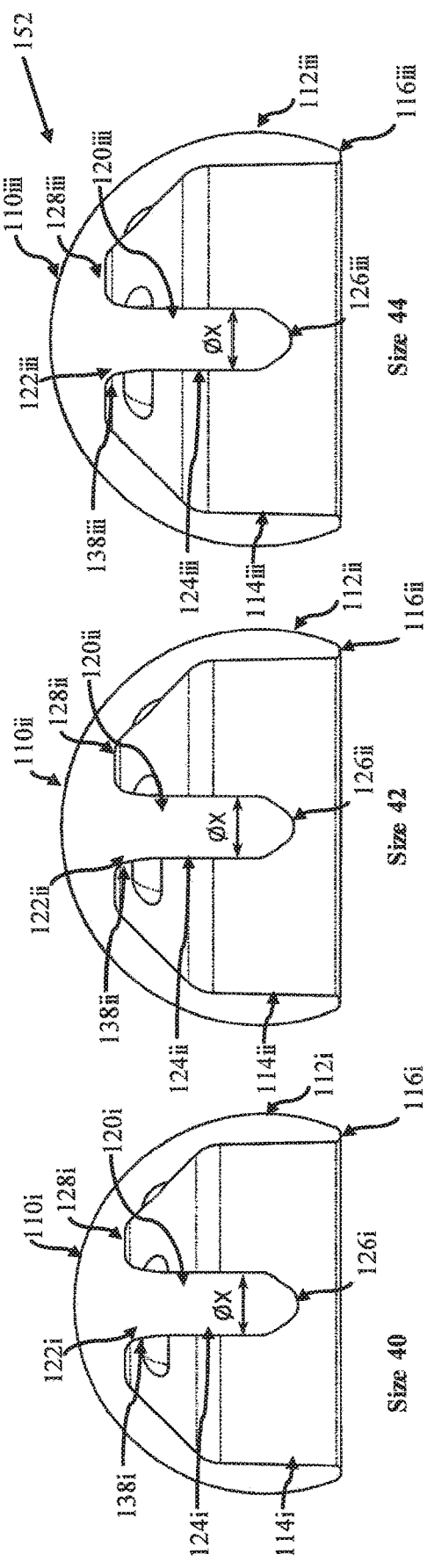

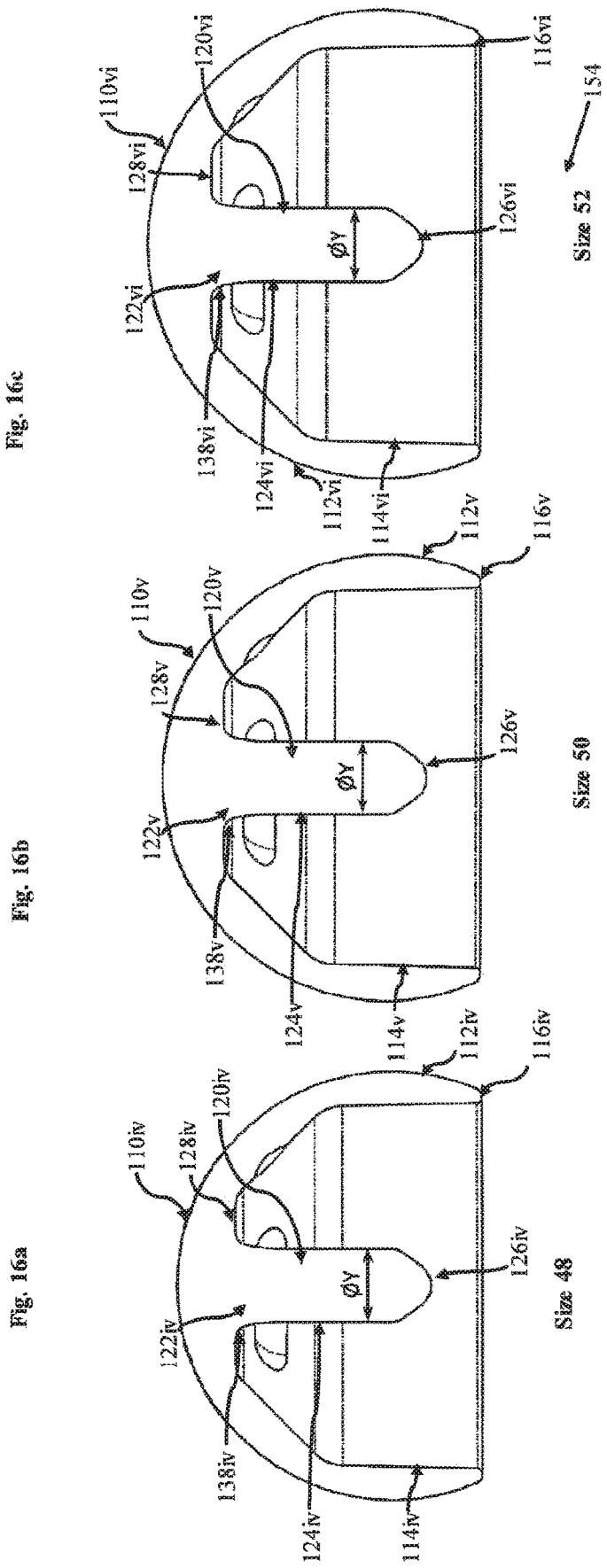

CERAMIC FEMORAL RESURFACING HEAD PROSTHESIS

The present invention relates to a ceramic femoral resurfacing head prosthesis for use in hip resurfacing procedures. The invention further relates to a method of increasing a fixation-land area of a ceramic femoral resurfacing head and a femoral resurfacing head prosthesis system for selective engagement of a femoral resurfacing head prosthesis with a resected femur based on one or more characteristics of the resected femur.

Femoral resurfacing has been developed as an alternative to conventional total hip replacement in a procedure for the treatment of arthritis of the hip, a condition which causes considerable pain and loss of movement. The hip is a ball and socket joint which allows the upper leg to move from side to side, back to front, and to rotate. The joint is made up of the head of the femur, the ball, which fits into the acetabulum, the socket. In a healthy hip, both the head of the femur and acetabulum are covered with cartilage which provides a smooth surface allowing the joint to move freely.

In general, femoral resurfacing involves the process of capping the head of the femur with a femoral resurfacing head prosthesis, attaching the prosthesis via bone cement, and fitting an acetabular cup to the acetabulum, generally using cementless fixation via a Titanium and/or Hydroxyapatite plasma coating. The femoral resurfacing head prosthesis and acetabular cup are conventionally formed from metal. A femoral resurfacing head prosthesis 10 in accordance with the state of the art is shown in FIGS. 1 to 5 and typically comprises a substantially spherical convex outer contact surface 12, a concave inner fixation surface 14, a rim 16 between the two surfaces defining an opening 18 and a stem 20 projecting from the concave inner fixation surface 14 and through the opening 18.

It has been found that a metal-on-metal resurfacing can result in the production of metal ions and subsequent diffusion or transport of the metal ions to the bloodstream or locality surrounding the hip replacement prosthesis. The presence of metal ions can result in allergic reaction or other adverse health effects for the patient.

Additionally, there is a risk of partial or total detachment of the femoral resurfacing head prosthesis from the underlying bone cement, if the adhesion or bonding between them is insufficient. Therefore, an increase in the area of overlap between an inner surface of a femoral resurfacing head prosthesis to the femur is desired, in order to increase the adhesion and thus minimise said risk. Further, by maximising the bone volume within the head prosthesis, bone resorption that can occur from stress shielding may be minimised.

The present invention seeks to provide a solution to these problems.

According to a first aspect of the present invention, there is provided a ceramic femoral resurfacing head prosthesis comprising: a ceramic convex outer contact surface engagable with an acetabulum of a patient or an acetabular cup prosthesis; a concave inner fixation surface having an inner-land portion, the ceramic convex outer contact surface and the concave inner fixation surface extending to intersect each other at a rim; and a ceramic stem projecting from the concave inner fixation surface, the stem adapted to be received by a stem bore, wherein a free distal end of the stem is at, or spaced inwardly of, a plane defined by the said rim, wherein the concave inner fixation surface includes a skirt between the inner-land portion and the rim of the head prosthesis, the skirt being cylindrical or substantially cylindrical, or frusto-conical or substantially frusto-conical, and at least one circumferentially elongate recess at the skirt to prevent or inhibit pull-off removal of the head prosthesis.

The use of ceramic is advantageous as the production of potentially hazardous metal ions is prevented or limited, given the reduction in the amount of metal used for the prosthesis. Additionally, ceramics are typically harder than most metals and therefore the wear of the prosthesis can be reduced compared to a typical arrangement, resulting in an increased longevity of the prosthesis. Hip resurfacing prostheses typically are not formed from ceramic as ceramics are generally brittle by nature and fracture can be unpredictable.

A free distal end of the stem being at, or spaced inwardly of, the rim results in a shorter stem than in a typical or conventional metal resurfacing arrangement. A shorter stem results in a reduced moment acting about the base of the stem and/or at any given point along the stem. This therefore reduces the amount of stress acting at or adjacent to the base and therefore improves the stress characteristics at or adjacent the base. The improvement and/or relative lack of degradation of the stress characteristics at the base of the stem is key for the present invention given its formation from ceramic, rather than metal as is conventional, given that, in general, ceramic has a lower ductility than metal. The risk of mechanical failure of the stem, and thus of the entire prosthesis, is thus reduced. Additionally, as the stem does not project beyond the rim, the prosthesis adopts a shape which substantially saves material. The device is therefore more conveniently and cheaply produced through green machining and sintering, a method typically used for the production of ceramic components. Lastly, the shorter stem results in a shorter stem bore being required to be drilled for implantation and therefore improves bone conservation.

The concave inner fixation surface may have a plurality of anti-rotation elements spaced around a circumference thereof. The ceramic stem may include at least a two-part angular transition in a longitudinal direction of the stem to meet the inner fixation surface such that the inner-land portion of the inner fixation surface at or adjacent to the stem is increased. The at least two-part angular transition may define a curve in a longitudinal direction of the stem having a non-uniform radius.

The at least two-part angular transition may include a first curved part having a radius in a range of 5 mm to 150 mm, a second curved part having a radius in a range of 10 mm to 100 mm, and a third curved part having a radius in a range of 0.5 mm to 2 mm. More preferably, the first curved part has a radius of or substantially of 50 mm, the second curved part has a radius of or substantially of 17.5 mm, and the third curved part has a radius of or substantially of 1.5 mm.

The first and second curved parts and the second and third curved parts may be contiguous with each other. The at least two-part angular transition may include at least one flat in a longitudinal direction of the stem. The at least two-part angular transition may be or may include a catenary curve. The circumferentially elongate recess may be an endless channel.

A rim of the ceramic femoral resurfacing head prosthesis defines an asymmetrical profile between the inner fixation surface and the outer contact surface with two or more different arcs having a radius in a range of 0.2 mm to 1.5 mm.

According to a second aspect of the present invention, there is provided a femoral resurfacing head prosthesis comprising: a ceramic convex outer contact surface engagable with an acetabulum of a patient or an acetabular cup prosthesis; a concave inner fixation surface, the ceramic convex outer contact surface and the concave inner fixation surface extending to intersect each other at a rim; and a ceramic stem projecting from the concave inner fixation surface and adapted to be received by a stem bore, wherein a free distal end of the stem is at, or spaced inwardly of, a plane defined by the said rim, wherein the concave inner fixation surface has a plurality of anti-rotation elements spaced around a circumference thereof. Preferably, one or more of the plurality of anti-rotation elements have the form of a discontinuous indentation, discontinuous recess and/or discontinuous groove.

According to a third aspect of the present invention, there is provided a ceramic femoral resurfacing head prosthesis comprising: a ceramic convex outer contact surface engagable with an acetabulum of a patient or an acetabular cup prosthesis; a concave inner fixation surface having an inner-land portion, the ceramic convex outer contact surface and the concave inner fixation surface extending to intersect each other at a rim; and a ceramic stem projecting from the concave inner fixation surface and adapted to be received by a stem bore, wherein a free distal end of the stem is at, or spaced inwardly of, a plane defined by the said rim, wherein the concave inner fixation surface includes a skirt between the inner-land portion and the rim of the head prosthesis, the skirt being cylindrical or substantially cylindrical, or frusto-conical or substantially frusto-conical, at least one circumferentially elongate recess at the skirt to prevent or inhibit pull-off removal of the head prosthesis, and a plurality of anti-rotation elements spaced around a circumference thereof.

According to a fourth aspect of the present invention, there is provided a ceramic femoral resurfacing head prosthesis comprising: a ceramic convex outer contact surface engagable with an acetabulum of a patient or an acetabular cup prosthesis; a concave inner fixation surface, the ceramic convex outer contact surface and the concave inner fixation surface extending to intersect each other at a rim; and a ceramic stem projecting from the concave inner fixation surface and adapted to be received by a stem bore, wherein a free distal end of the stem is at, or spaced inwardly of, a plane defined by the said rim, wherein the ceramic stem includes at least a two-part angular transition in a longitudinal direction of the stem to meet the concave inner fixation surface such that an inner-land portion of the concave inner fixation surface at or adjacent to the ceramic stem is increased, the at least a two-part angular transition defining a curve in a longitudinal direction of the stem having a non-uniform radius.

According to a fifth aspect of the present invention, there is provided a ceramic femoral resurfacing head prosthesis comprising: a ceramic convex outer contact surface engagable with an acetabulum of a patient or an acetabular cup prosthesis; a concave inner fixation surface, the ceramic convex outer contact surface and the concave inner fixation surface extending to intersect each other at a rim; and a ceramic stem projecting from the concave inner fixation surface and adapted to be received by a stem bore, wherein a free distal end of the stem is at, or spaced inwardly of, a plane defined by the said rim, wherein the ceramic stem includes at least a two-part angular transition in a longitudinal direction of the stem to meet the concave inner fixation surface such that an inner-land portion of the concave inner fixation surface at or adjacent to the ceramic stem is increased, the two-part angular transition being or including a catenary curve.

According to a sixth aspect of the present invention, there is provided a ceramic femoral resurfacing head prosthesis comprising: a ceramic convex outer contact surface engagable with an acetabulum of a patient or an acetabular cup prosthesis; a concave inner fixation surface; a ceramic stem projecting from the inner fixation surface, the stem adapted to be received by a stem bore; a base portion of the stem comprising at least a two-part angular transition in a longitudinal direction of the stem to meet the inner fixation surface, thereby increasing an inner-land portion of the inner fixation surface at or adjacent to the stem.

The extension of the inner-land portion of the inner fixation surface increases an area of overlap between the inner fixation surface and the in use resected head of the femur, to which the ceramic femoral resurfacing head prosthesis is attached. This allows for an increase in an area of contact between in use bone cement or other bonding agent, typically applied between the prosthesis and the femur to adhere the prosthesis to the femur, and the inner fixation surface. An increase in the area of contact can increase the adhesion, and therefore the risk of failure of the resurfacing by detachment of the prosthesis from the femur is reduced. The longevity of the replacement may thus be increased.

Preferably, the concave inner fixation surface has a plurality of anti-rotation elements spaced around a circumference thereof. The at least two-part angular transition may define a curve in a longitudinal direction of the stem having a non-uniform radius.

The at least two-part angular transition may include a first curved part having a radius in a range of 5 mm to 150 mm, a second curved part having a radius in a range of 10 mm to 100 mm, and a third curved part having a radius in a range of 0.5 mm to 2 mm. The first curved part may have a radius of or substantially of 50 mm, the second curved part has a radius of or substantially of 17.5 mm, and the third curved part has a radius of or substantially of 1.5 mm. Preferably, the first and second curved parts and the second and third curved parts are contiguous with each other.

The at least two-part angular transition may include at least one flat in a longitudinal direction of the stem. Preferably, the at least two-part angular transition is or includes a catenary curve.

The concave inner fixation surface may include at least one circumferentially elongate recess for surgical bone cement interdigitation to prevent or inhibit pull-off removal of the head prosthesis.

The circumferentially elongate recess may be an endless channel. The inner fixation surface may include a skirt between the inner-land portion and a rim of the head prosthesis, the circumferentially elongate recess being at the skirt.

Preferably, the outer contact surface and the inner fixation surface extend to intersect each other at a or the rim, and a free distal end of the stem is at or spaced inwardly of a plane defined by the said rim. A or the rim may define an asymmetrical profile between the inner fixation surface and the outer contact surface with two or more different arcs having a radius in a range of 0.2 mm to 1.5 mm. A or the rim may include at least an outer radius to the convex outer contact surface equal to or greater than 0.5 mm.

Preferably, the anti-rotation elements comprise one or more indentations on the inner fixation surface to receive a surgical bone cement. One or more of the anti-rotation elements may have the form of a discontinuous semi-toroidal indentation on the inner fixation surface. The anti-rotation elements may be equi-angularly spaced apart on the inner fixation surface. Preferably, at least one anti-rotation element includes a multipart indentation having a plurality of anti-rotation zones. Each anti-rotation zone may be demarcated from the other anti-rotation zones by discontinuities in depth of the indentation at their respective boundary. Preferably, each anti-rotation element has a central anti-rotation zone, and a plurality of non-central anti-rotation zones adjacent to the central anti-rotation zones. Preferably, at least two non-central anti-rotation zones are separated from each other by the central anti-rotation zone. The central anti-rotation zone may comprise a majority of the volume of the indentation.

According to a seventh aspect of the present invention, there is provided a method of increasing a fixation-land area of a ceramic femoral resurfacing head without or without substantially detrimentally affecting a stress characteristic at or adjacent to an associated stem, the method comprising the step of forming a stem of a ceramic femoral resurfacing head prosthesis in accordance with the first aspect of the invention with at least a two-part angular transition in a longitudinal direction thereof to meet an inner fixation surface.

A two-part angular transition enables a first curved part to have a smaller or tighter radius of curvature, and a second curved part to have a greater radius of curvature, than the radius of curvature of the transition between the stem and the inner fixation surface for a typical or conventional femoral resurfacing head. A smaller radius of curvature allows for a sharper or more abrupt transition between the inner fixation surface and the longitudinal extent of the stem which enables an increase in the extent of the inner fixation surface. A second curved part having a greater bend radius reduces a stress concentration at the base of the stem. As such, the stress characteristic adjacent to the stem is not detrimentally affected, and the risk of mechanical failure of the stem is not increased compared to currently known transitions of metal resurfacing heads, given that the ceramic generally has a lower ductility compared to typical metal compositions.

A radial extent of the at least two-part angular transition may be unbisectable. The at least two-part angular transition may be defined by two different curves. The at least two-part angular transition may be defined by a flat and a curve in a longitudinal direction of the stem.

According to an eighth aspect of the present invention, there is provided a femoral resurfacing head prosthesis system for selective engagement of a femoral resurfacing head prosthesis with a resected femur based on one or more characteristics of the resected femur, the femoral resurfacing head prosthesis system comprising: a first group of ceramic femoral resurfacing head prostheses, each ceramic femoral resurfacing head prosthesis of the first group having a first convex outer contact surface with a predetermined geometry which is different to the others within the first group, the first convex outer contact surface being engageable with an acetabulum of a patient or an acetabular cup prosthesis; a first inner fixation surface adapted to be engaged with a femur of the patient; and a first stem projecting from the first inner fixation surface, the first stem having a first lateral extent adapted to be receivable by a stem bore, the first lateral extent being common to the first group; and at least a second group of ceramic femoral resurfacing head prostheses, each ceramic femoral resurfacing head prosthesis of the second group having a second convex outer contact surface with a predetermined geometry which is different to the others within the second group, the second convex outer contact surface being engagable with an acetabulum of a patient or an acetabular cup prosthesis; a second inner fixation surface adapted to be engaged with a femur of the patient; and a second stem projecting from the second inner fixation surface, the second stem having a second lateral extent adapted to be receivable by a stem bore, the second lateral extent being common to the second group and different to the first group; one said ceramic femoral resurfacing head prosthesis from the first or second groups being selectively engagable with the resected femur based on the one or more characteristics thereof.

Providing a first and second group of ceramic femoral resurfacing head prostheses, each prosthesis within each group having a convex outer contact surface having a different pre-determined geometry to every other prosthesis within the same respective group, allows for the geometry and/or dimensions of the convex outer contact surface to be more closely matched to the geometry and/or dimensions of the acetabulum of a patient, without necessitating patient-specific construction of each ceramic femoral resurfacing head prosthesis. Advantageously, the prostheses of each of the first group and the second group respectively may have a common second lateral extent, the common second lateral extent of the first group being different to the common second lateral extent of the second group, so that a surgeon or other medical practitioner may select a second lateral extent suitable to the patient's anatomy while reducing the variation of dimension of stem bore that the surgeon may be required to form.

The first convex outer contact surface of each ceramic femoral resurfacing head prosthesis of the first group may have a different equatorial circumference to that of the other ceramic femoral resurfacing head prosthesis in the first group. The second convex outer contact surface of each ceramic femoral resurfacing head prosthesis of the second group may have a different equatorial circumference to that of the other ceramic femoral resurfacing head prosthesis in the second group. The ceramic femoral resurfacing head prostheses of the first and second groups each may have different equatorial circumferences. A length and/or diameter of the first and second stems may be different.

Preferably, a rim of each ceramic femoral resurfacing head prosthesis of the first and second groups defines an asymmetrical profile between the inner fixation surface and the outer contact surface with two or more different arcs having a radius in a range of 0.2 mm to 1.5 mm. The outer contact surface and the inner fixation surface may extend to intersect each other at a or the rim, and a free distal end of the stem may be at or spaced inwardly of a plane defined by the said rim. The first and/or second inner fixation surfaces may include at least one circumferentially elongate recess to prevent or inhibit pull-off removal of the head prosthesis.

According to a ninth aspect of the present invention, there is provided a ceramic femoral resurfacing head prosthesis comprising: a ceramic convex outer contact surface engagable with an acetabulum of a patient or an acetabular cup prosthesis; a concave inner fixation surface, the outer contact surface and the inner fixation surface extending to intersect each other at a rim; a ceramic stem projecting from the inner fixation surface and adapted to be received by a stem bore, wherein a free distal end of the stem is at, or spaced inwardly of, a plane defined by the said rim.

The concave inner fixation surface may have a plurality of anti-rotation elements spaced around a circumference thereof. The ceramic stem may include at least a two-part angular transition in a longitudinal direction of the stem to meet the inner fixation surface such that an inner-land portion of the inner fixation surface at or adjacent to the stem is increased.

The at least two-part angular transition may define a curve in a longitudinal direction of the stem having a non-uniform radius. The at least two-part angular transition may include a first curved part having a radius in a range of 5 mm to 150 mm, a second curved part having a radius in a range of 10 mm to 100 mm, and a third curved part having a radius in a range of 0.5 mm to 2 mm. The first curved part may have a radius of or substantially of 50 mm, the second curved part has a radius of or substantially of 17.5 mm, and the third curved part has a radius of or substantially of 1.5 mm. The first and second curved parts and the second and third curved parts may be contiguous with each other. The at least two-part angular transition may include at least one flat in a longitudinal direction of the stem. The at least two-part angular transition may or may include a catenary curve.

The concave inner fixation surface may include at least one circumferentially elongate recess to prevent or inhibit pull-off removal of the head prosthesis. The circumferentially elongate recess may be an endless channel. The inner fixation surface may include a skirt between the inner-land portion and a rim of the head prosthesis, the circumferentially elongate recess being at the skirt. A rim of the ceramic femoral resurfacing head prosthesis may define an asymmetrical profile between the inner fixation surface and the outer contact surface with two or more different arcs having a radius in a range of 0.2 mm to 1.5 mm.

According to a tenth aspect of the present invention, there is provided a ceramic femoral resurfacing head prosthesis comprising: a ceramic convex outer contact surface engagable with an acetabulum of a patient or an acetabular cup prosthesis; a concave inner fixation surface, the outer contact surface and the inner fixation surface extending to intersect each other at a rim; a ceramic stem projecting from the inner fixation surface and adapted to be received by a stem bore, wherein the rim defines an asymmetrical profile between the inner and outer contact surfaces with two or more different arcs having a radius in a range of 0.2 mm to 1.5 mm.

The rim having an asymmetrical profile with two or more different arcs allows for the width of the rim to be increased, by reducing a longitudinal extent of the ceramic femoral resurfacing head prosthesis, whilst simultaneously maximising the inner fixation surface and reducing the risk of damage to an external edge portion of the rim on implantation and/or in use. The width of the rim is increased as compared to a conventional femoral resurfacing head prosthesis by reducing the longitudinal extent of the ceramic femoral resurfacing head prosthesis while maintaining the dimensions of the outer contact surface.

An asymmetric profile enables a radius of curvature of an external edge of the rim to be greater than the radius of curvature of the external edge of the rim of a conventional prosthesis. Furthermore, a radius of curvature of an internal edge of the rim, due to the asymmetry, may be the same or similar as the radius of curvature of a conventional prosthesis, for example. The similar internal edge curvature maximises the inner fixation surface by maintaining the abruptness or sharpness of the transition between the inner fixation surface and the rim, and the gradual, greater radius of curvature of the external edge reduces the risk of damage to the rim by reducing stress concentration adjacent to the external edge rim.

The concave inner fixation surface may have a plurality of anti-rotation elements spaced around a circumference thereof. The rim may include at least an outer radius to the convex outer contact surface equal to or greater than 0.5 mm. A free distal end of the stem may be at, or spaced inwardly of, a plane defined by the said rim.

Preferably, the ceramic stem includes an at least two-part angular transition in a longitudinal direction of the stem to meet the inner fixation surface such that an inner-land portion of the inner fixation surface at or adjacent to the stem is increased. The at least two-part angular transition may define a curve in a longitudinal direction of the stem having a non-uniform radius. The at least two-part angular transition may include a first curved part having a radius in a range of 5 mm to 150 mm, a second curved part having a radius in a range of 10 mm to 100 mm, and a third curved part having a radius in a range of 0.5 mm to 2 mm. The first curved part may have a radius of or substantially of 50 mm, the second curved part has a radius of or substantially of 17.5 mm, and the third curved part has a radius of or substantially of 1.5 mm. The first and second curved parts and the second and third curved parts may be contiguous with each other.

The at least two-part angular transition may include at least one flat in a longitudinal direction of the stem. The at least two-part angular transition may be or include a catenary curve. The concave inner fixation surface may include at least one circumferentially elongate recess to prevent or inhibit pull-off removal of the head prosthesis. The circumferentially elongate recess may be an endless channel. The inner fixation surface may include a skirt between the inner-land portion and a rim of the head prosthesis, the circumferentially elongate recess being at the skirt.

According to an eleventh aspect of the present invention, there is provided a ceramic femoral resurfacing head prosthesis comprising: a ceramic convex outer contact surface engagable with an acetabulum of a patient or an acetabular cup prosthesis; a concave inner fixation surface, the outer contact surface and the inner fixation surface extending to intersect each other at a rim; a ceramic stem projecting from the inner fixation surface and adapted to be received by a stem bore; and at least one circumferentially elongate recess at the concave inner fixation surface to promote surgical bone cement interdigitation and prevent or inhibit pull-off removal of the head prosthesis.

Pull-off of the head prosthesis after the hip resurfacing surgery had been completed would result in a failure of the prosthesis and thus pain and/or a reduction in mobility of the patient. Further surgery would be necessitated to correct the issue. Therefore, a circumferentially elongate recess increases or maintains a longevity of the resurfaced hip joint.

The concave inner fixation surface may have a plurality of anti-rotation elements spaced around a circumference thereof. The circumferentially elongate recess may be an endless channel. The inner fixation surface may include a skirt between the inner-land portion and a rim of the head prosthesis, the circumferentially elongate recess being at the skirt.

The rim may define an asymmetrical profile between the inner and outer contact surfaces with two or more different arcs having a radius in a range of 0.2 mm to 1.5 mm. The rim may include at least an outer radius to the convex outer contact surface equal to or greater than 0.5 mm. A free distal end of the stem may be at, or spaced inwardly of, a plane defined by the said rim.

The ceramic stem may include an at least two-part angular transition in a longitudinal direction of the stem to meet the inner fixation surface such that an inner-land portion of the inner fixation surface at or adjacent to the stem is increased. The at least two-part angular transition may define a curve in a longitudinal direction of the stem having a non-uniform radius. The at least two-part angular transition may include a first curved part having a radius in a range of 5 mm to 150 mm, a second curved part having a radius in a range of 10 mm to 100 mm, and a third curved part having a radius in a range of 0.5 mm to 2 mm. The first curved part may more preferably have a radius of or substantially of 50 mm, the second curved part has a radius of or substantially of 17.5 mm, and the third curved part has a radius of or substantially of 1.5 mm. The first and second curved parts and the second and third curved parts may be contiguous with each other. The at least two-part angular transition may include at least one flat in a longitudinal direction of the stem.

The at least two-part angular transition may be or may include a catenary curve.

The invention will now be more particularly described, by way of example only, with reference to the accompanying drawings, in which.

Figure 1:
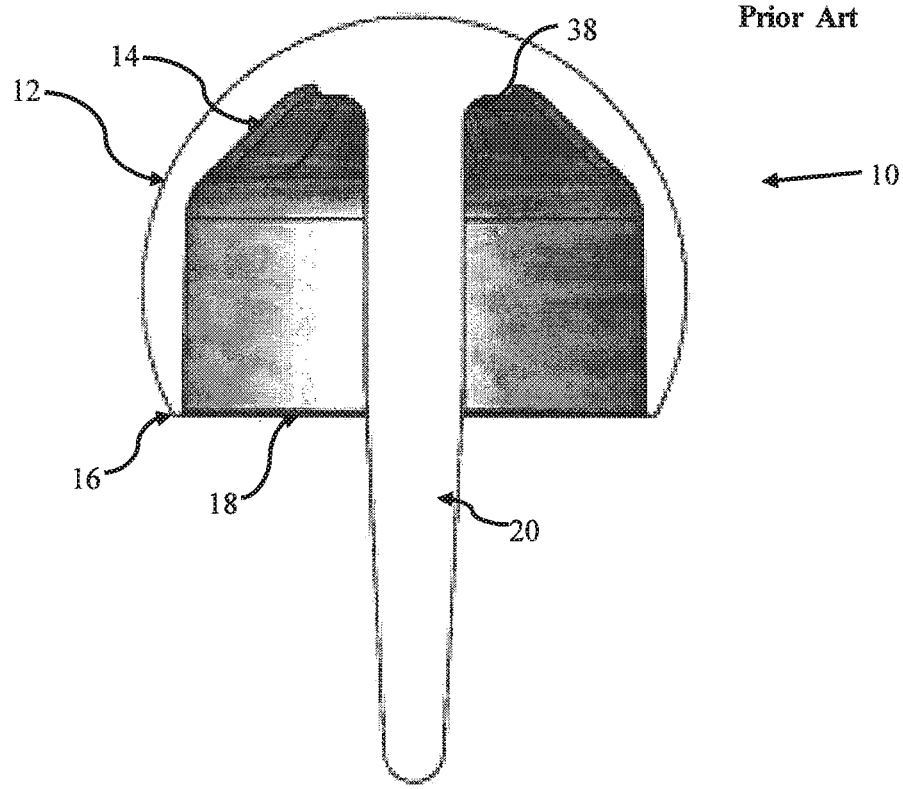
FIG. 1 shows a radial cross-section of a femoral resurfacing head prosthesis in accordance with the state of the art.
Figure 2:
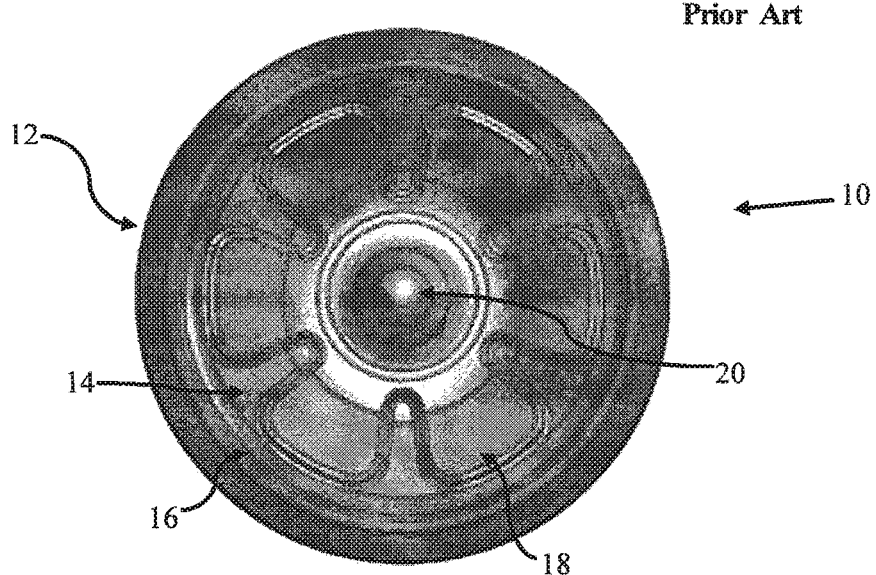
FIG. 2 shows a representation of the femoral resurfacing head prosthesis of FIG. 1 from a distal end of a stem.

FIGS. 15a, 15b and 15c show second, third and fourth embodiments of the ceramic femoral resurfacing head prosthesis each embodiment being adapted for a first group of the system in accordance with the third aspect of the present invention; and FIGS. 16a, 16b and 16c show fifth, sixth and seventh embodiments of the present invention in accordance with each embodiment being adapted for a second group of the system in accordance with the third aspect of the present invention.

Referring to FIGS. 6 to 14 there is shown a ceramic femoral resurfacing head prosthesis 110 comprising a ceramic convex outer contact surface 112, which is or is a substantially spherical surface and is generally a segment of a sphere slightly greater than a hemisphere, and a concave inner fixation surface 114.

Although the outer contact surface and the inner fixation surface are described as being convex and concave respectively, it is appreciated that one or both surfaces may in fact not be concave or convex and/or may be at least in part planar or multifaceted, as necessity dictates.

The ceramic convex outer contact surface 112 and the concave inner fixation surface 114 are preferably contiguous and meet at a rim 116 which thereby forms a plane and a circular or substantially circular opening 118. In this way, the rim may be planar or substantially planar.

A ceramic stem 120 projects from the concave inner fixation surface 114, preferably opposite or substantially opposite from the opening 118. The ceramic stem 120 may have a base portion 122 proximal to and at or adjacent to the concave inner fixation surface 114, a cylindrical or a substantially cylindrical shaped body portion 124 and a frustoconical or substantially frustoconical shaped distal free end 126, or tip portion, distal to the concave inner fixation surface 114 and the base portion 122, the body portion 124 separating the base portion 122 form the distal free end 126.

A longitudinal extent of the ceramic stem 120 is such that the distal free end 126 is at or spaced inwardly of the plane defined by the rim 116. The ceramic stem 120 is therefore shorter than the stem 20 of the prior art femoral resurfacing head prosthesis; a direct comparison of the two stems can be seen in FIGS. 15a to 15c and 16a to 16c. Whilst the extent of the ceramic stem is so described, it is appreciated that the longitudinal extent of the stem may be such that the distal free end of the stem extends beyond the plane defined by the rim.

The base portion 122 of the ceramic stem 120 merges, substantially merges or transitions into the concave inner fixation surface 114 and the concave inner fixation surface 114 preferably has an inner-land 128 which here may be at or adjacent to base portion 122 such that it may be considered to extend around a circumferential extent of, surround, encircle and/or be adjacent to the base portion 122. The inner-land 128 is preferably planar or substantially planar and may be transverse, lateral or perpendicular or substantially perpendicular to a longitudinal extent of the ceramic stem 120. Whilst described as encircling the base portion, it is appreciated that the inner-land may only extend around part of the circumferential extent the base portion.

Adjacent to the inner-land 128, an intermediary portion 130 of the concave inner fixation surface 114 may extend at an angle to the plane of the inner-land 128, and preferably at an obtuse angle. This arrangement is such that the intermediary portion 130 and the inner-land 128 together substantially form the shape of an external surface of a frustocone with a base removed.

A plurality of, and preferably three as shown, anti-rotation elements 132 may be equiangularly arranged around a circumferential extent of the concave inner fixation surface 114, and more specifically the intermediary portion 130. Each anti-rotation element 132 may here be formed as an indentation, recess or groove in the concave inner fixation surface 114 and a longitudinal extent of the indentation, recess or groove may be aligned with a circumferential extent of the intermediary portion 130. The anti-rotation elements 132 are preferably spaced apart, i.e. discontinuous from one another, to prevent rotation around a circumferential extent of the concave inner fixation surface 114. Here, preferably each anti-rotation element 132 may be elongate and may have at least one rounded edge. Each of the anti-rotation elements 132 may have the form of a discontinuous semi-toroidal indentation. This toroidal indentation is such that a radial profile of the anti-rotation element 132 may be a circular or semi-circular.

Additionally, whilst described as being circumferentially aligned elongate indentations, recesses or grooves, it is appreciated that anti-rotation elements may take other forms, for example each anti-rotation element may be a circular recess or may be a projection. Furthermore, at least one of the anti-rotation elements may include a multipart indentation having a plurality of anti-rotation zones and each anti-rotation zone may be demarcated from the other anti-rotation zones by discontinuities in depth of the indentation at their respective boundary. Each anti-rotation element may have a central anti-rotation zone and a plurality of non-central anti-rotation zones adjacent to the central anti-rotation zone. Although described and shown as being positioned in the intermediary portion, it is appreciated that the anti-rotation elements may in fact be positioned elsewhere on concave inner fixation surface, for example on the inner-land area 128. It is also appreciated that the ceramic femoral resurfacing head prosthesis may not necessarily include a or any anti-rotation elements.

The concave inner fixation surface 114 may further comprise a skirt 134 positioned between the rim 116 and the inner-land 128, and more specifically between the rim 116 and the intermediary portion 130. The skirt 134 is preferably annular in shape and an axial extent of the annular shaped skirt 134 may extend parallel or substantially parallel to a longitudinal extent of the ceramic stem 120. Whilst described as extending parallel to the ceramic stem 120, it is appreciated that the axial extent of the skirt 134 may in fact extend at an angle and towards the stem and as such the skirt 134 may be considered to taper or narrow in diameter towards the rim 116. Alternatively, the axial extent of the skirt 134 may in fact extend at an angle and away from the stem such that the skirt 134 may be considered to widen in diameter towards the rim 116. The skirt 134 is preferably cylindrical or substantially cylindrical, or frusto-conical or substantially frusto-conical.

The skirt 134 may preferably further comprise at least one circumferentially elongate recess 136 or groove in the concave inner fixation surface 114, preferably extending around a circumferential extent of the concave inner fixation surface 114 and/or skirt 134. The elongate recess 136 may be an endless channel, although it is appreciated that the recess may not be endless and may only extend around a portion of the extent of concave inner fixation surface. Additionally, there may be a plurality of circumferentially aligned and substantially coplanar elongate recesses 136 positioned in the skirt 134 which individually extend around a portion of the circumference of the skirt 134.

The merging and/or transition of the base portion 122 of the ceramic stem 120 with or to the inner-land 128 of the concave inner fixation surface 114 is preferably at least a two-part angular transition 138. Each part of the at least two-part angular transition 138 preferably has a different radius or radius of curvature such that a radial extent of the at least two-part angular transition is unbisectable. The radius of curvature of each curved part is therefore different. The curved parts are not symmetrical about a plane which separates adjacent said curved parts. One or more of the curved parts may also not be symmetrical about a line which bisects the said curved part. The unbisectability of the radial extent of the at least two-part angular transition 138 is shown by sectioning line B1 in FIG. 9, which does not bisect the two-part angular transition 138. By contrast the bisectability of the radial extent of the single angular transition 38 of the prior art is shown by bisection line B2 in FIG. 4.

Figure 3:
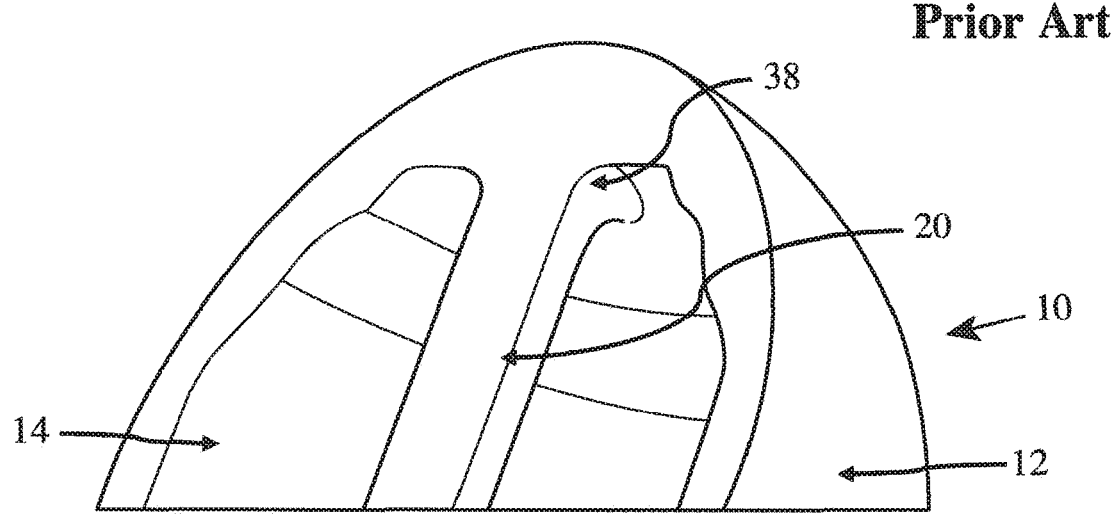
FIG. 3 is a perspective representation of the radial cross-section of FIG. 1 with stress distribution indicated, stress is here indicated by colour with green indicating low stress and red indicating high stress.
Figure 4:
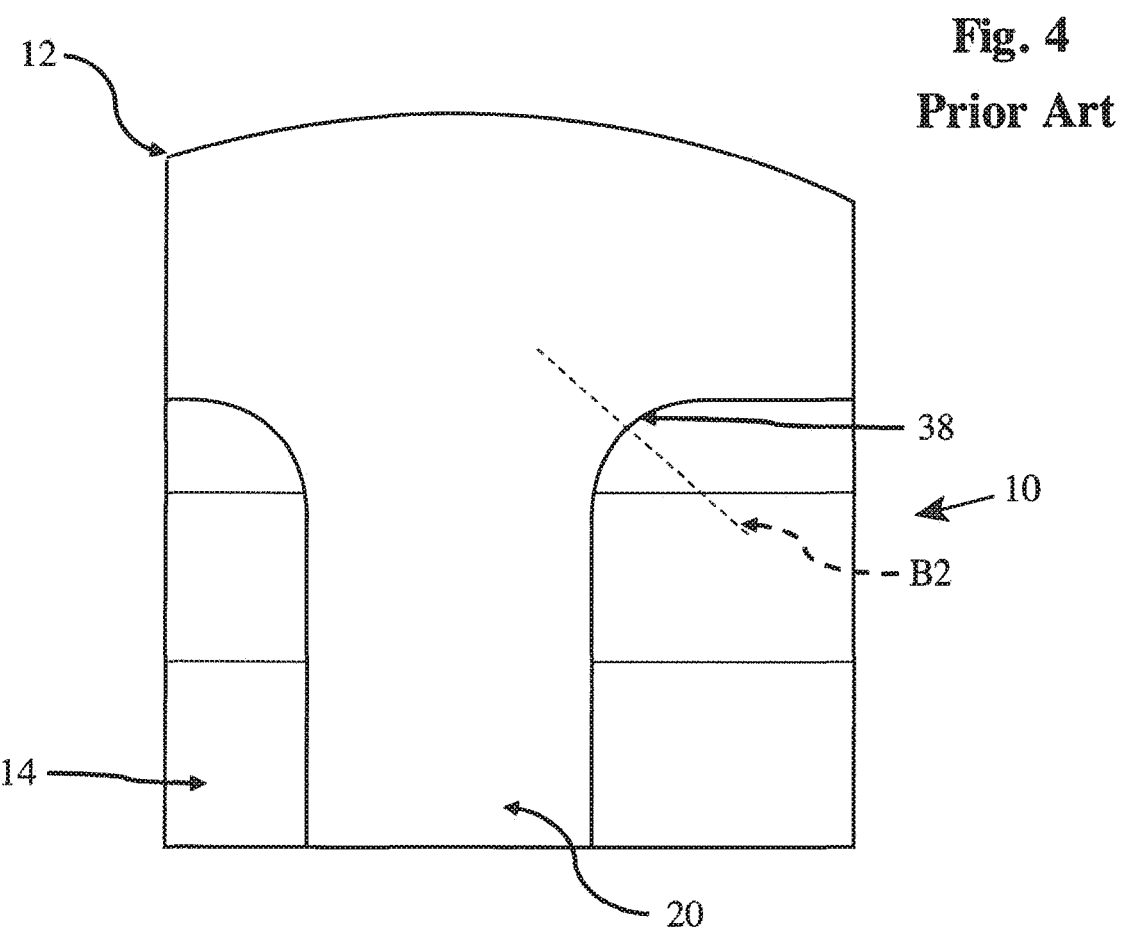
FIG. 4 shows an enlarged view of FIG. 1, showing the interconnection of a stem and an inner fixation surface, stress is here indicated by colour with green indicating low stress and red indicating high stress.
Figure 9:
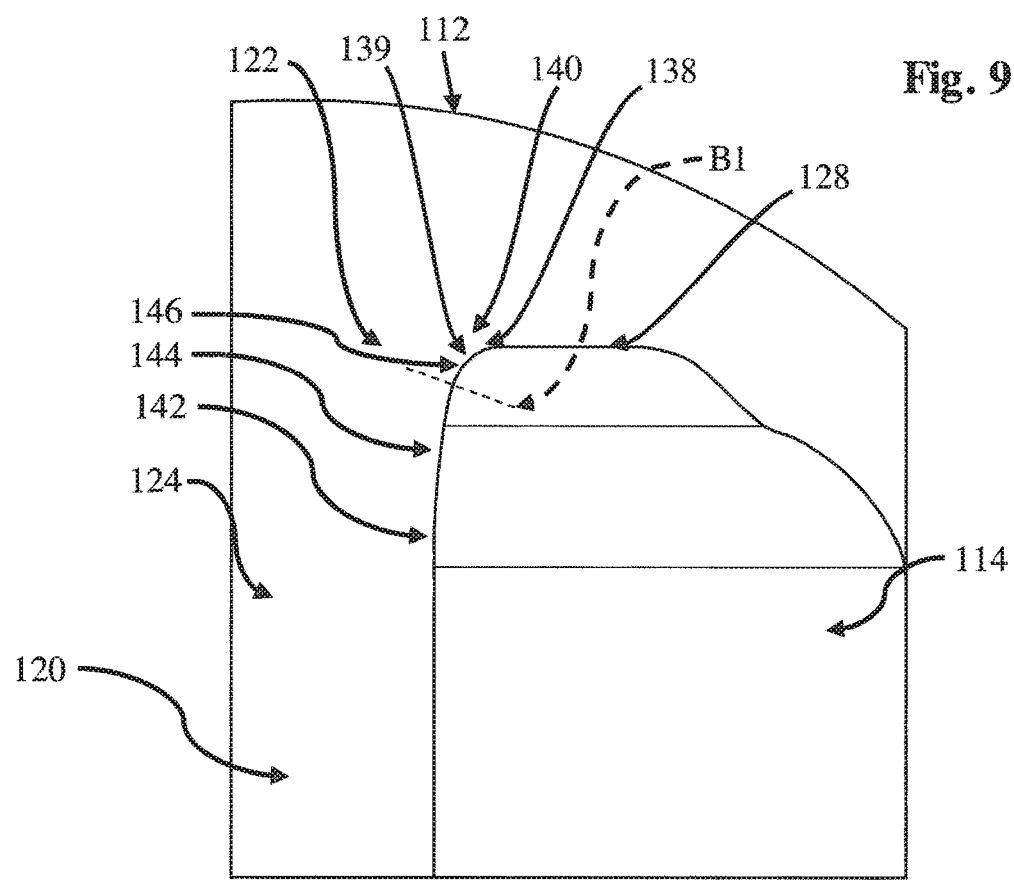
FIG. 9 shows the radial cross-section of the femoral resurfacing head prosthesis in FIG. 8, enlarged and showing the interconnection of a stem and an inner fixation surface, with stress concentration indicated by colour: green indicating low stress and red indicating high stress.

Therefore, the at least two-part angular transition 138 preferably defines a curve in an axial or longitudinal direction or extent of the stem 120 having a non-uniform radius. Most preferably, as shown in FIG. 9, the at least two-part angular transition 138 is a three-part angular transition 140. The two- or three-part transition 138, 140 preferably extends uniformly around the circumferential extent of the base portion 122 of the ceramic stem 120. This is such that the base portion 122 of the stem 120 may be considered to be hyperbolic frustocone or a frustocone having a nonuniform pitch, with the wider base of the frustocone being adjacent to the inner-land 128. A direct comparison between the transition of the present invention and the transition 38 of the prior art can be seen in FIG. 10. The transition in accordance with the state of the art is also shown in FIGS. 3 and 4.

The three-part angular transition 140 preferably firstly comprises a first curved part 142. The first curved part 142 is an axial extent of the base portion 122 of the stem 120 being at or adjacent to the cylindrical body portion 124 having a constant, uniform or regular radius of curvature, referenced at R1 in FIG. 10. The curvature of R1 is preferably such that it curves away from an axial direction of the stem 120. The radius of curvature R1 is preferably in the range of 5 mm to 150 mm and more preferably may be at, around or substantially 50 mm. Although being described as having a constant, uniform or regular radius of curvature, it is appreciated that the first curved part may be flat, and thus have an undefinable radius of curvature, in an axial or longitudinal extent of the stem, or may be irregularly or non-uniformly curved. In the instance of being flat, an axial cross-section of the first curved part may be considered to be straight. Whilst the radius of curvature of the first part is given as preferably having an upper limit, it is appreciated that the radius of curvature may in fact only preferably be greater than 5 mm.

The three-part angular transition 140 further comprises a second curved part 144. The second curved part 142 is on an axial extent of the base portion 122 of the stem 120 being adjacent to and contiguous with the first curved part 142 and is distal to the cylindrical body portion 124 as compared to the first curved part 142, having a radius of curvature referenced R2 in FIG. 10. The radius of curvature of the second curved part 144 may preferably be in the range of 10 mm to 100 mm, may more preferably be in the range of 10 mm to 25 mm, may most preferably be in the range of 15 mm to 20 mm, and may be at, around or substantially 17.5 mm. Although, the second curved part 144 is described as being a curve having a radius of curvature of the above values, it is appreciated that the curve may in fact be a catenary curve thus having no singular radius of curvature.

Alternatively, the second curved part may in fact be flat in an axial or longitudinal extent of the stem, and thus have an undefinable radius of curvature in an axial or longitudinal extent of the stem. In this instance, an axial cross-section of the second curved part may be considered to be straight. Lastly the second curved part may have parabolic character or have any irregular or non-uniform curvature. Whilst the radius of curvature of the second part is given as preferably having an upper limit, it is appreciated that the radius of curvature may in fact only preferably be greater than 10 mm.

The three-part angular transition 140 lastly comprises a third curved part 146, having a radius of curvature labelled R3. The third curved part 146 is on and axial extent of the base portion 122 of the stem 120 being inter-positioned between and at or adjacent to both of the inner-land 128 portion and second curved part 144. The third curved part 146 may preferably have a constant, uniform or regular radius of curvature R3. The radius of curvature R3 of the third curved part 146 may preferably in the range of 0.5 mm to 2 mm, and more preferably may be at, around or substantially 1.5 mm. Although being described as having a constant, uniform or regular radius of curvature, it is appreciated that the third curved part may be flat, and thus have an undefinable radius of curvature in an axial or longitudinal extent of the stem or may be irregularly or non-uniformly curved. In the instance of the third curved part being flat, an axial cross-section of the third curved part may be considered to be straight. Whilst the radius of curvature of the third part is given as preferably having an upper limit, it is appreciated that the radius of curvature may in fact only preferably be greater than 0.5 mm.

Whilst the at least two-part angular transition 138 is described as having three angular transitions, with the first and second curved parts 142, 144 being contiguous with each other and the second and third parts 144, 146 being contiguous with each other, it is appreciated that it may in fact only have two angular transitions or may have more than three angular transitions. Whilst the above values for the radius of curvatures of the curved part are specified, it should be noted that the advantage provided by the at least two-part angular transition 138 is given by having at least two contiguous curved parts; a curved part adjacent to the stem and a curved part adjacent to the inner-land 128, the curved part adjacent to the inner-land 128 having a tighter or smaller radius of curvature than the radius of curvature of the curved part adjacent to the stem. The above values of radius of curvature R1, R2, R3 may vary and/or scale depending on the dimensions of the other features of the ceramic femoral resurfacing head prosthesis 110, particularly a diameter of the ceramic outer contact surface 112. Alternatively, the above values may not vary and/or scale depending on the dimensions of the ceramic of the other features of the ceramic femoral resurfacing head prosthesis 110.

It is appreciated that the transition may in fact not extend uniformly around the circumferential extent of the base and the number of curved parts or radius of curvature of each part of the transition may vary depending on its circumferential position. It is further noted that the ceramic femoral resurfacing head prosthesis 110 may in fact have a singular angular transition, for example, the curved part 38 in the state of the art having a radius of curvature of 2.5 mm and indicated by R4 in FIG. 10.

Figure 10:
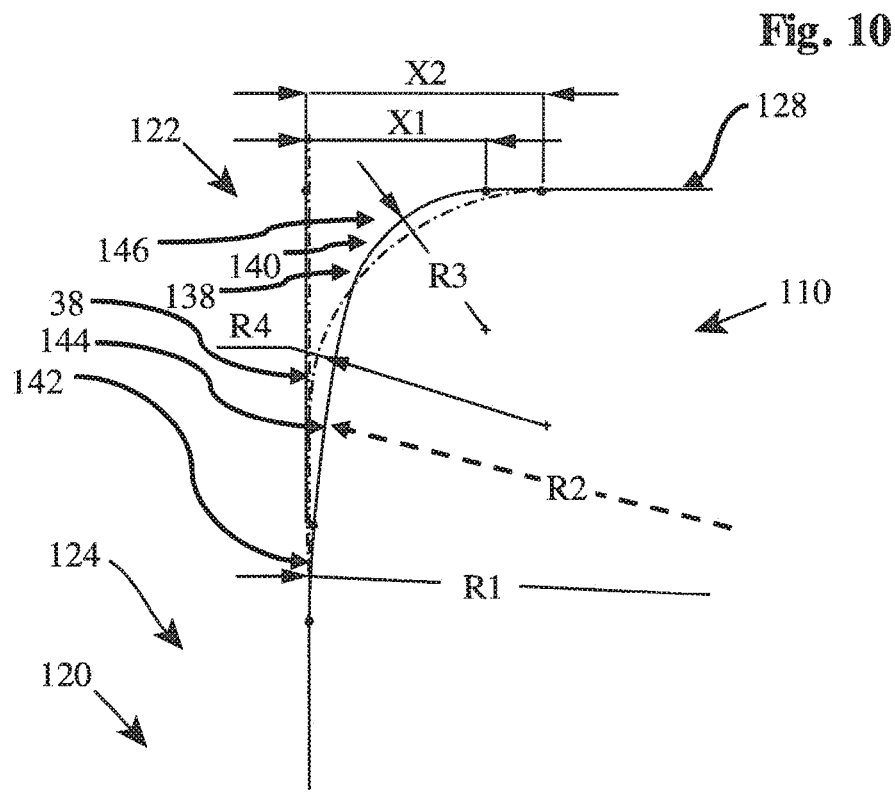
FIG. 10 is a similar view of the femoral resurfacing head prosthesis shown in FIG. 9, but showing in broken line a prior-art uniform-radius transition between the stem and the inner fixation surface, as well as in overlaid solid line a multi-part transition between the stem and the inner fixation surface according to the present invention.
Figure 11:
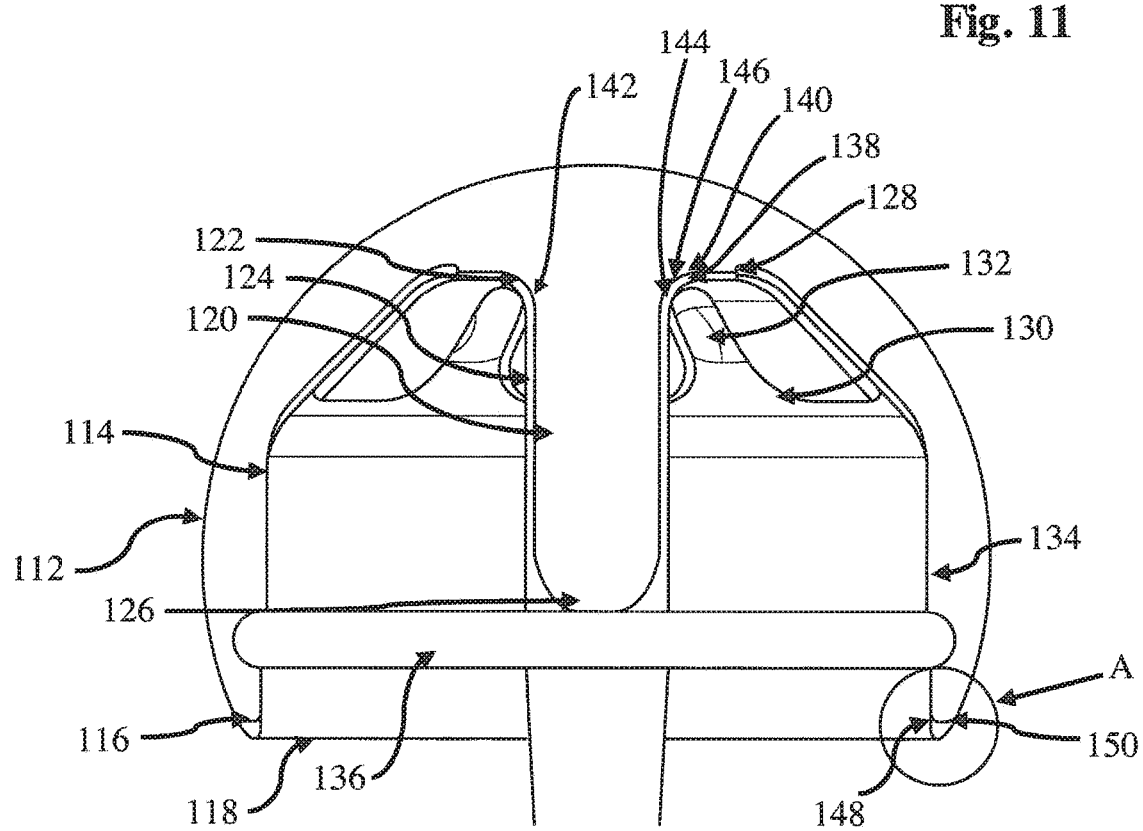
FIG. 11 shows an axial cross-section of the femoral resurfacing head prosthesis of the present invention overlying an axial cross-section of the prior-art resurfacing head, the different cross-sections being indicated by different colours with the femoral resurfacing head prosthesis of the present invention being shown in pink, and the prior-art device being shown in grey.
Figure 12:
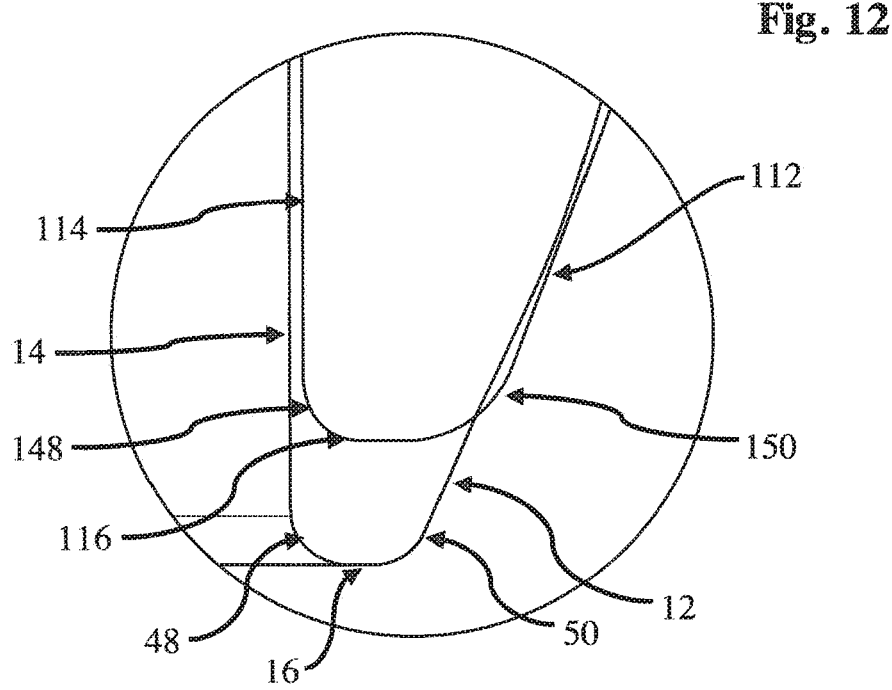
FIG. 12 shows an enlargement of a portion of the rim of the femoral resurfacing head prosthesis, referenced by circle A in FIG. 11.

The three-part angular transition 140 is so arranged to maximise the surface area of the inner-land 128, by decreasing the lateral extent over which the transition 140 extends, whilst maintaining, improving, or restricting or limiting a degradation of in use stress characteristics, such as stress concentration, adjacent to the base 124 of the ceramic stem 120 as compared to the prior art. This is achieved by having a third curved part 146 with a smaller radius of curvature than the radius of curvature R4 of the prior art, allowing the transition or merging between the stem 120 and the inner-land 128 to occur more proximal to the stem 120. Any negative affect to the stress characteristics by this tighter radius of curvature is mitigated by having second and/or first curved parts 142, 144 having a radius of curvature greater than the prior art and greater than the third curved part 146 which reduces stress concentration. This increase of inner-land 128 whilst maintenance of suitable stress characteristics is demonstrated by a comparison of FIGS. 4 and 9. The lateral extent of the transition 140 between the stem 120 and the inner-land 128 is indicated in FIG. 10 by X1 for the present invention and X2 in the prior art. Given that X1 is smaller than X2, the inner-land 128 can be shown to be extended and increased in area in the present invention as compared to the prior art.

The rim 116 preferably has an asymmetrical profile, the asymmetric profile may be considered to be a lateral profile of the rim 116. The asymmetrical profile of the rim 116, and a comparison to the symmetrical rim 116 of the prior art, may be seen in FIGS. 12 to 14.

The rim 116 here has an inner, or internal, edge 148 and an outer, or external, edge 150, both edges 148, 150 preferably extending around a circumferential extent of the rim 116 and thus the ceramic femoral resurfacing head prosthesis 110. The outer edge 150 may be proximal to the ceramic convex outer contact surface 112 and the inner edge 148 may be proximal to the concave inner fixation surface 114. Both the inner edge 148, and the outer edge 150 may be considered to be curved or substantially curved, the inner edge 148 having a radius of curvature labelled R5 in FIG. 14 and similarly R6 for the outer edge 150. The radius of curvature of the inner edge 148 is preferably smaller than the radius of curvature of the outer edge 150. The radius of curvature of the inner edge 148 may preferably be in a range of 0.2 mm and 1.5 mm and may more preferably be at, around or substantially 0.5 mm. The radius of curvature of the outer edge 150 is preferably in the range of 0.5 mm and 2 mm, and more preferably being at, around or substantially 1 mm. Whilst the above values are specified, it should be appreciated that the radius of curvature may vary depending on the overall size of the ceramic femoral resurfacing head prosthesis 110 and that the importance of this part of the present invention is that the radius of curvature of the outer edge 150 is greater than the radius of curvature of the inner edge 148. A substantially flat or planar portion may interspace the inner and outer edges 148, 150.

Figure 5:
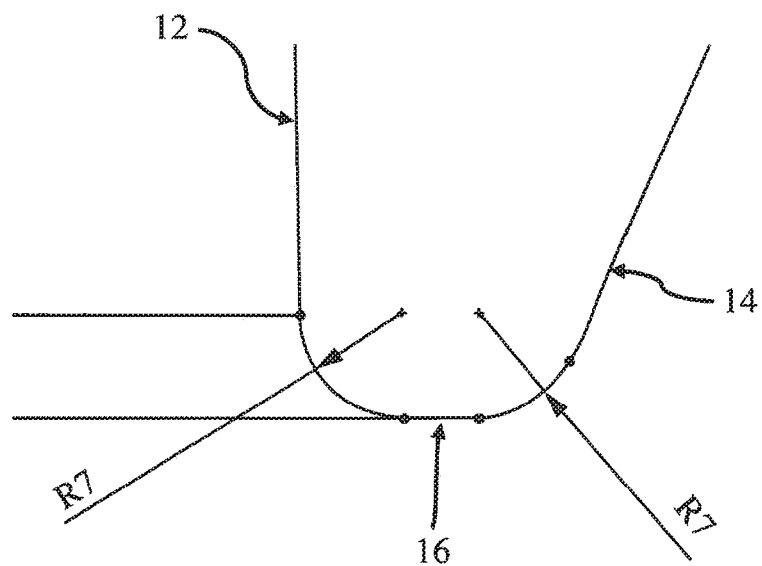
FIG. 5 shows an enlarged view of FIG. 1, showing a rim of the femoral resurfacing head prosthesis, with the value of the radius of curvature of the internal and external edges of the rim indicated.
Figure 6:
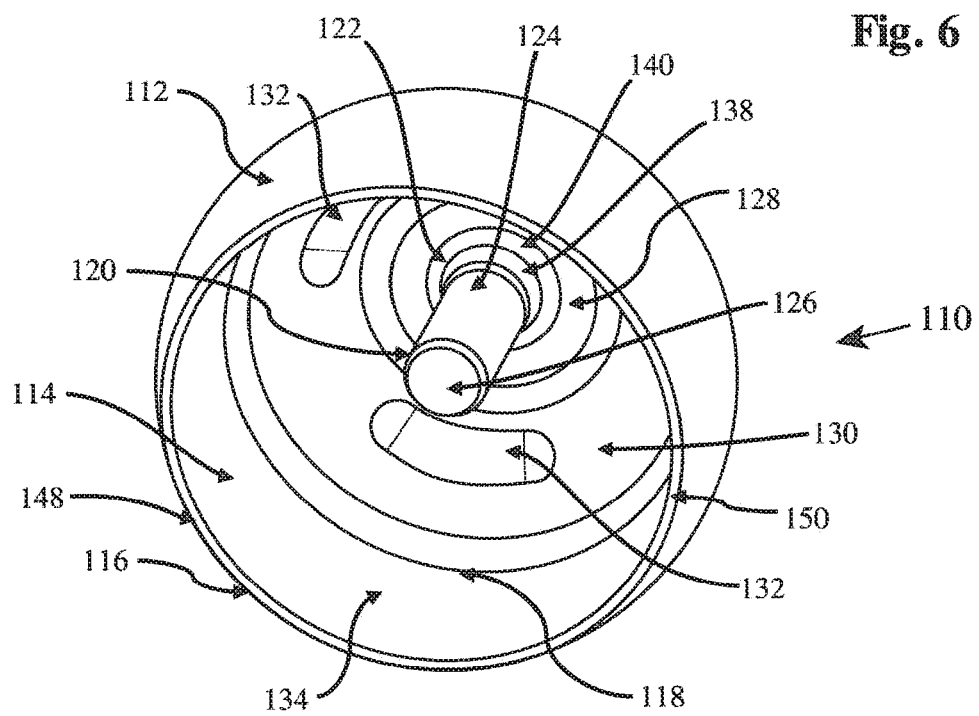
FIG. 6 shows a perspective representation of a first embodiment of a femoral resurfacing head prosthesis, in accordance with the first, fourth, fifth and sixth aspects of the present invention and specifically adapted for the method in accordance with the second aspect of the present invention.
Figure 7:
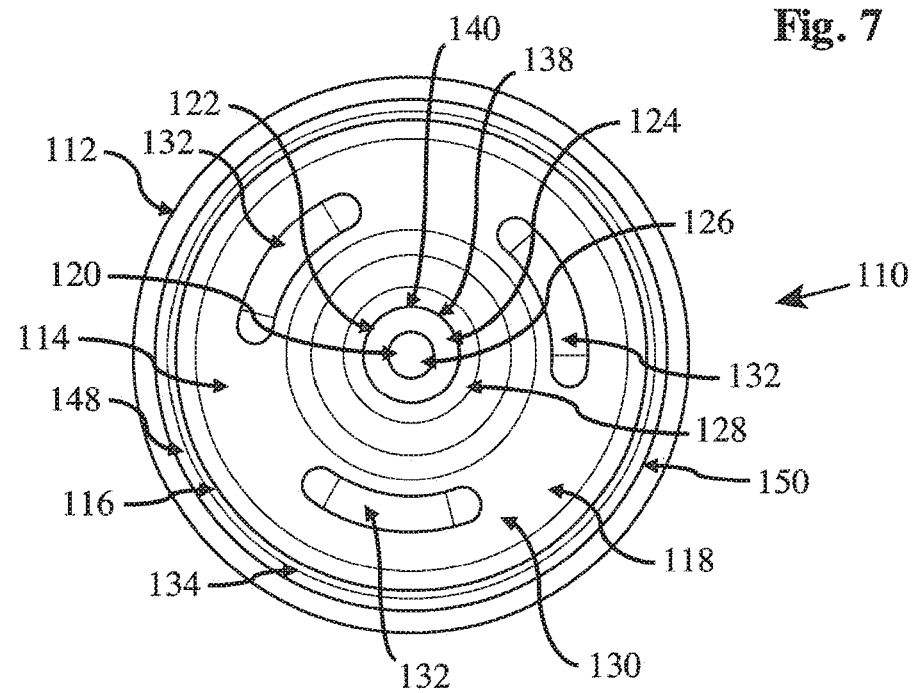
FIG. 7 shows a representation of the femoral resurfacing head prosthesis of FIG. 6 from a distal end of a stem.
Figure 8:
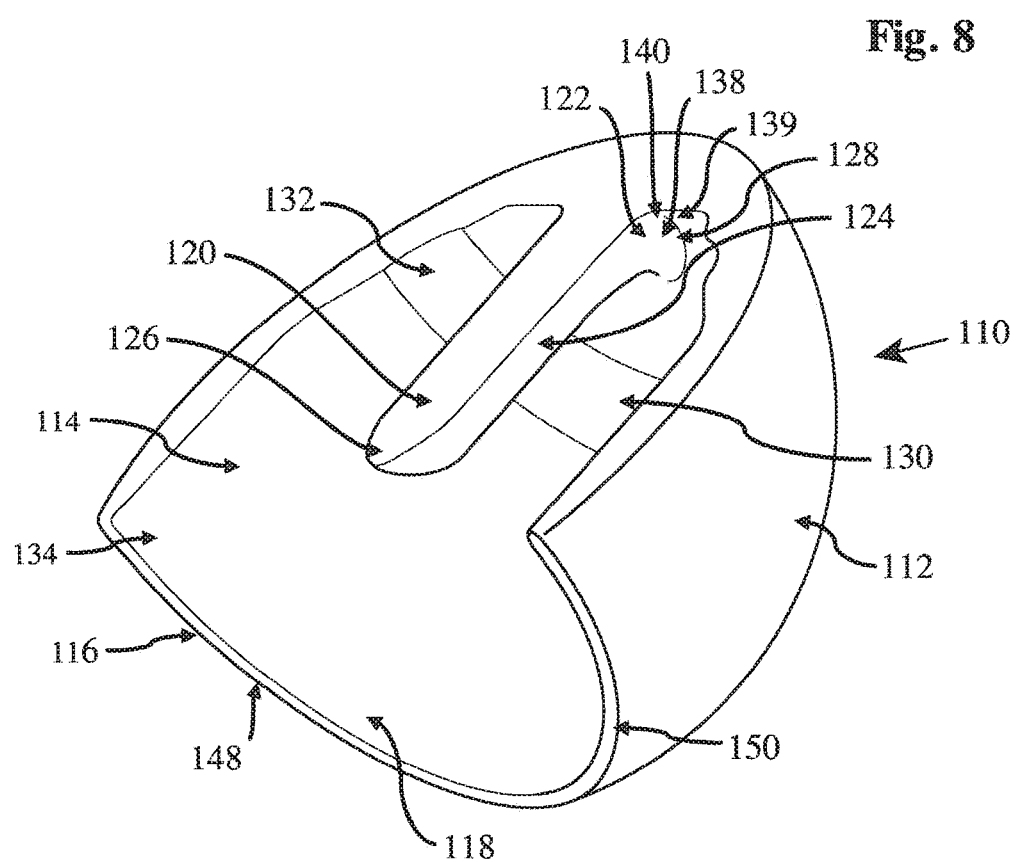
FIG. 8 shows a perspective representation of a radial cross-section of the femoral resurfacing head prosthesis, with stress distribution indicated; stress is here indicated by colour, with green indicating low stress and red indicating high stress.
Figure 13:
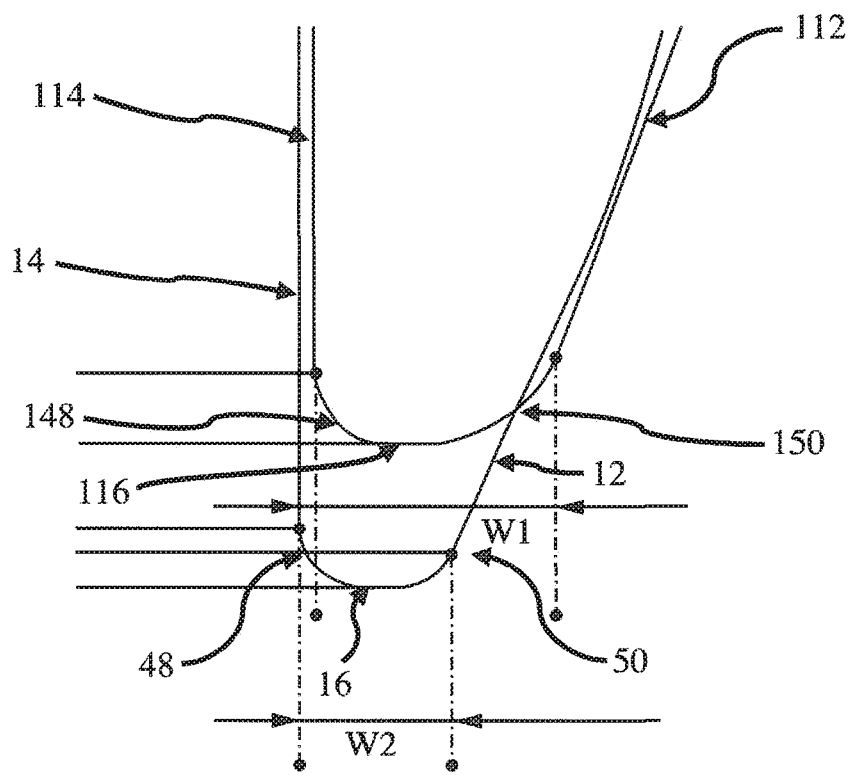
FIG. 13 shows the enlarged portion of the rim, shown in FIG. 12, with the width of the rim of the present invention overlying a portion of the rim of the prior-art head.
Figure 14:
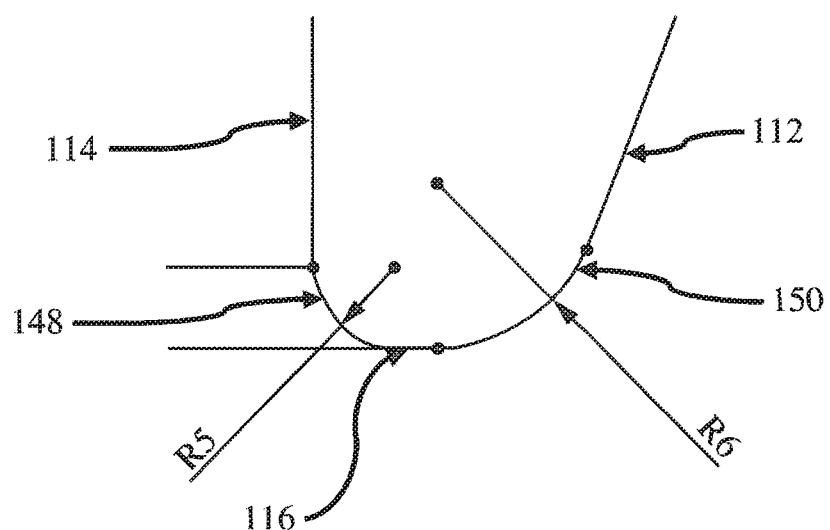
FIG. 14 shows the enlarged portion of the rim of the femoral resurfacing head prosthesis shown in FIGS. 12 and 13, with a comparison of inner and outer lateral rim-edge radii.

The effect of the lateral profile of the rim 116 being asymmetrical is that the rim 116 may be thickened, when compared to the prior art, by the axial extent of the ceramic femoral resurfacing head prosthesis 110 being reduced, but the concave inner fixation surface 114 may still be maximised. The smaller inner radius of curvature R5 maximises the concave inner fixation surface 114 by reducing the axial extent of the transition between the inner surface 114 and the distal surface of the rim 116. The larger outer radius of curvature R6 reduces stress concentration and therefore reduces the risk of fracture or failure of part of this component, when compared to a smaller or typical radius of curvature. The contrasting symmetrical profile, and therefore equal radius of curvature for both the inner and outer edge 48, 58 of the rim 16 in the prior art can be seen in FIG. 5 where the radius of curvature of both edges is labelled as R7. This radius of curvature can also be seen in FIGS. 12 and 13 where the profiles of both rims 16, 116 are shown overlain. The increase in width of the rim 116 of the present invention over the prior art is illustrated in FIG. 13 by a comparison of W1, a width of the rim of the present invention, with W2, a width of the rim of the prior art.

Whilst the profile of the rim 116 of the ceramic femoral resurfacing head prosthesis 110 is here described as being asymmetrical, it is appreciated that it may in fact be symmetrical, for example similar to or the same as the profile of the rim 16 in the prior art.

The ceramic femoral resurfacing head prosthesis 110 may preferably be wholly made from ceramic; however, it is appreciated that ceramic femoral resurfacing head prosthesis may only partly be made from ceramic and that selected components, such as the stem 120, may not be made from ceramic. The ceramic selected for use in the ceramic femoral resurfacing head prosthesis 110 may preferably be inert to the human body and should have a high hardness to reduce wear. Ceramics suitable for use may in particular be zirconia toughened alumina but also alumina, zirconia, activated alumina, bioglass, silicon nitride, zirconia or any other ceramic.

Whilst the rim 116 is here described as forming a plane it is appreciated that the rim 116 may not be substantially planar and may undulate, for example having the form of a wave or having a sinusoidal or substantially sinusoidal circumferential extent. In the event that the rim 116 is not planar, a plane defined by the rim 116 may be taken to be the extent of the rim 116 furthest from, closest to or at a mean distance of the rim from the inner-land portion 120. Additionally or alternatively, whilst the plane defined by the rim 116 is shown as being perpendicular to the longitudinal extent of the ceramic stem 120, it is appreciated that the rim may not perpendicular to the longitudinal extent of the ceramic stem 120. For example, the plane defined by the rim may be at an angle to the ceramic stem 120, due to an asymmetrical longitudinal extent of the skirt 134.

Referring to FIGS. 15a to 15c, there are shown variations of the first embodiment of the ceramic femoral resurfacing head prosthesis 110 together forming a first group 152 of ceramic femoral resurfacing head prostheses 110. Referring to FIGS. 16a to 16c, there are shown variations of the first embodiment of the ceramic femoral resurfacing head prosthesis 110 together forming a second group 154 of ceramic femoral resurfacing head prostheses 110. Although only first and second groups 152, 154 are described, it will be clear that more than two groups having the characteristics outlined hereinafter can be provided, where necessity dictates.

Each prosthesis variation of the first embodiment may be at least in part distinguished by a differing equatorial diameter of the convex outer contact surface 112 for each ceramic femoral resurfacing head prosthesis 110. The equatorial diameter of the convex outer contact surface 112 in mm for each variation of first embodiment is given below each figure as a size. For example, "Size 40" refers to an equatorial diameter of substantially 40 mm. These variants on the present invention are the same as the preceding embodiment with the exception that the dimensions of the stem as compared to the ceramic convex outer contact surface 112 may differ. Elements which are similar or identical to those of the preceding embodiment are denoted by the same reference number with i to vi added to denote a variation, and further detailed description is omitted.

Across the first group 152, a lateral extent of the ceramic stem 120i may be constant, common or uniform or substantially constant, common or uniform along at least a majority of a longitudinal extent of the stem. Given that the lateral extent of each stem 120i may not be constant along an entire longitudinal extent thereof, due at least to the tapering at the distal free end portion 126i and the at least two-part angular transition 138i of the base portion 122i, the said lateral extent which is constant across the group may be taken from a same or similar longitudinal reference point for each ceramic stem 120i of a first group 152.

The longitudinal reference point may, for example, be within a longitudinal extent of the body portion 124i, the body portion of each ceramic stem preferably having a constant or substantially constant lateral extent therealong. Alternatively, the longitudinal reference point may be taken to be at the base of the ceramic stem 120i or between the inner-land 128i and the body portion 124i.

The constant or substantially constant lateral extent of each ceramic stem 120i within the first group 152 may at least be along part of the longitudinal extent of each ceramic stem 120i and may preferably be constant or substantially constant along a majority of each ceramic stem 120i of a group. Whilst a lateral extent of each ceramic stem 120i is constant, a longitudinal extent of each stem 120i may vary across the group 152. This varying longitudinal extent may be achieved by varying only the longitudinal extent of the body portion 124i of each stem 120i, in this way a longitudinal and lateral extent of the base portion 122i and the distal free end portion 126i of each stem within the group 152 may be constant or common. Alternatively, the length of the ceramic stem may be varied by also or only varying the longitudinal extent of the base portion 122i, including the at least two-part angular transition 138i, and/or the distal free end portion 126i. Given the non-constant lateral extent of the base portion 122i or distal free end portion 126i, by varying their longitudinal extent the lateral extent of the ceramic stem 120i may vary at these portions and thus the lateral extent of each ceramic stem 120i within a group may not be constant along the entirety of the longitudinal extent of the stem 120i. In the event that a lateral cross-section of the ceramic stem 120i is not circular, the major or largest lateral dimension of the lateral extent should be constant, common or uniform across a group, in the same or similar way as described above.

The at least two-part angular transition 138i may be the same for each ceramic stem 120i of each ceramic femoral resurfacing head prosthesis 110i within the first group 152. Alternatively, the at least two-part angular transition 138i may be different for each ceramic stem 120i of each ceramic femoral resurfacing head prosthesis 110i within the first group 152. This difference may be due to differing radii of curvature for each or any of the curved parts of the two-part angular transition 138 across each femoral resurfacing head prosthesis 110i of the first group 152.

Although the longitudinal extent of each ceramic stem 120i is described as varying across a first group 152, it is appreciated that the longitudinal extent of each ceramic stem 120i may also remain constant, common or uniform or substantially constant, common or uniform.

The lateral extent of the ceramic stem 120i may be in the range of 5 mm to 7.5 mm, and more preferably may be at, around or substantially 6.6 mm. The lateral extent of the first group 152 may be given by OX in FIGS. 15a to 15c. The dimensions of the remainder of the features of each of the femoral resurfacing head prosthesis may vary, especially the ceramic convex outer contact surface 112i, the concave inner fixation surface 114i and even a length of the stem. As such, each ceramic femoral resurfacing head prosthesis 110i may have a different equatorial circumference to that of the other ceramic femoral resurfacing head prostheses 110*i* of the first group 152. Therefore, the ceramic stems of all of the ceramic femoral resurfacing head prostheses 110*i* of a first group 152 may be individually selectively co-operable with a given, and the same, stem bore, also known as the femoral bore.

In the same or similar way as above, within the second group 154, the lateral extent of the ceramic stem 120*iv* may be constant, common or uniform or substantially constant, common or uniform along at least part of the longitudinal extent of the ceramic stem. Within the second group 154, the said constant lateral extent may be taken at the same or similar longitudinal reference point as above. In the same or similar way as above, the longitudinal extent of each of the ceramic stems 120*iv* within the group 154 may vary or, alternatively, may not vary. Here the lateral extent of ceramic stem 120*iv* may be in the range of 7 mm to 9 mm, and more preferably may be at, around or substantially 8.1 mm and therefore may be generally greater than the lateral extent of the ceramic stem 120*i* of the first group 152. The lateral extent of the second group 154 is given by ØY in FIGS. 16*a* to 16*c*. The dimensions of the remainder of the features of each of the femoral resurfacing head prosthesis may vary, especially the convex outer contact surface. The dimensions of said features of the second group 154, including the longitudinal extent of the stem 120*iv*, may also vary with respect to the dimensions of the said features of the first group 152. As such, each ceramic femoral resurfacing head prosthesis 110*iv* may have a different equatorial circumference and/or a different longitudinal extent of the stem, to that of the other ceramic femoral resurfacing head prosthesis 110*iv* of a second group 154 and of the first group 152.

The at least two-part angular transition 138*i* of the ceramic stem 120*i* of the first group 152 may be the same or similar to the at least two-part angular transition 138*iv* of the ceramic stem 120*iv* of the second group 154. Alternatively, the at least two-part angular transition 138*i* of the ceramic stem 120*i* of the first group 152 may be different to the at least two-part angular transition 138*iv* of the ceramic stem 120*iv* of the second group 154.

However, the lateral extent of the ceramic stem 120*iv* of the second group 154 is different to the ceramic stem 120*i* of the first group 152. Therefore, the ceramic stems of all of the ceramic femoral resurfacing head prostheses 110*iv* of a second group 154 may be individually selectively co-operable with a given, and the same, stem or femoral bore, but may not be individually selectively co-operable with a stem or femoral bore suitable for use with the first group 152 and vice versa.

Therefore, a range of prostheses having differing ceramic convex outer contact surfaces 112 and concave inner fixation surface 114, but all being suitable for insertion into a stem bore or femoral bore of the same dimensions, and in particular the same lateral dimension, may be selectable.

Whilst, as described, the only difference between the ceramic femoral resurfacing head prostheses 110 are the relative size of the lateral extent of the stem 120 compared to the other features, it is appreciated that within a group, for a given lateral extent of stem, there may be other variations. For example, there may be differing numbers of anti-rotation elements or no anti-rotation elements between the ceramic femoral resurfacing head prostheses of a group. Additionally, there may be more or different shaped or sized elongate recesses to promote adhesion to the head of the femur. Therefore, in use the surgeon may select from a group of femoral resurfacing head prostheses having a particular feature and having already prepared the stem bore during surgery.

A surgical procedure may be performed to in use apply the ceramic femoral resurfacing head prosthesis 110 to a patient. This may take the form of making an incision in the patient, adjacent to the hip. The surgical approach may be most commonly made posterior to the hip, however lateral, anterior, anterior-lateral and medial approaches are also possible. The head portion of the femur and the acetabulum are then exposed and the head of the femur may be dislocated from the acetabulum.

A ceramic femoral resurfacing head prosthesis 110 or femoral resurfacing head prosthesis group 152, 154 may be selected based on the size of the femur head and the size of the acetabulum or acetabular cup into which the femur is to be inserted. The head of the femur is then prepared and/or resected by shaping the femur so as to substantially correspond with the concave inner fixation surface 114 of the selected femoral resurfacing head prosthesis. This may involve removing an edge portion of the head of the femur using a chamfer-cutting tool.

A stem bore may be drilled into a longitudinal extent of the femur, the diameter and length of the bore to be drilled corresponding to the dimensions of the stem 120 of the femoral resurfacing head prosthesis 110 or femoral resurfacing head prosthesis group 152, 154 selected. If a group 152, 154 of femoral resurfacing head prostheses 110 has been selected then a single femoral resurfacing head prosthesis 110 is selected from that group which corresponds most closely with the size of the acetabulum or acetabular cup into which the resurfaced femur head is to be inserted.

Bone cement is then applied to the concave inner fixation surface 114 and/or the surface of the resected femur. The femoral resurfacing head prosthesis is then positioned over the resected femur and the ceramic stem 120 is inserted into the stem bore. The bone cement bonds or affixes the resected femur to the ceramic femoral head prosthesis. The optional anti-rotation elements 132 may be filled with cement and therefore prevent rotation of the femoral resurfacing head prosthesis. Similarly, the elongate recess 136 may also be filled with cement and thereby promote surgical bone cement interdigitation to prevent or inhibit pull-off removal of the head prosthesis 110. The resurfaced ceramic femoral head may then be inserted or impacted into the acetabulum or acetabular cup.

The acetabulum is then typically prepared to receive an in use acetabular cup by removing cartilage from and otherwise enlarging the acetabulum with a reamer. An in use acetabular cup, selected to correspond to the ceramic convex outer contact surface, is then inserted or impacted into the enlarged acetabulum and may be secured by using an adhesive such as bone cement.

The area around the hip may then be cleaned to remove any excess bone or cement, and the incision may be sealed.

It is appreciated that the above procedure may be performed in a reverse sequence and the above sequence of events is given for illustrative purposes only. For example, the procedure may clearly also be performed by first preparing the acetabulum or acetabular cup and then resurfacing the femoral head.

It is therefore possible to provide a ceramic femoral head prosthesis which, through a two- or more-part angular transition of the stem to increase an inner-land for improved bone engagement and support, has at least comparable stress characteristics at or adjacent to a base of the stem compared to presently known non-ceramic femoral head prostheses.

Furthermore, it is also possible to provide a ceramic femoral head prosthesis with a more robust rim to prevent or limit facture, chipping or breakage, thereby significantly improving longevity.

Additionally, it is possible to provide a ceramic femoral head prosthesis with an internal profile that improves engagement of the prosthesis with the femur through surgical bone cement interdigitation, thereby reducing a likelihood of the prosthesis unseating during patient use.

These features may be present in the ceramic femoral head prosthesis either individually or in any combination.

It is also possible to provide a system of two or more groups of selectable ceramic femoral head prostheses having different outer surface characteristics. By each group having a common ceramic stem dimension, profile or stem diameter, a number of tools required to fit the selected prosthesis may be reduced.

The words 'comprises/comprising' and the words 'having/including' when used herein with reference to the present invention are used to specify the presence of stated features, integers, steps or components, but do not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

The embodiments described above are provided by way of examples only, and various other modifications will be apparent to persons skilled in the field without departing from the scope of the invention as defined herein.

What is claimed is:

1. A ceramic femoral resurfacing head prosthesis comprising:
    a ceramic convex outer contact surface adapted to engage with an acetabulum of a patient or an acetabular cup prosthesis;
    a concave inner fixation surface, the ceramic convex outer contact surface and the concave inner fixation surface extending to intersect each other at a rim; and
    a ceramic stem projecting from the concave inner fixation surface and adapted to be received by a stem bore, wherein a free distal end of the stem is at, or spaced inwardly of, a plane defined by the said rim, wherein the ceramic stem includes at least a two-part angular transition in a longitudinal direction of the stem to meet the concave inner fixation surface such that an inner-land portion of the concave inner fixation surface at or adjacent to the ceramic stem is increased, the at least a two-part angular transition defining a curve in a longitudinal direction of the stem having a non-uniform radius.

2. The ceramic femoral resurfacing head prosthesis as claimed in claim 1, wherein the concave inner fixation surface has a plurality of anti-rotation elements spaced around a circumference thereof.

3. The ceramic femoral resurfacing head prosthesis as claimed in claim 2, wherein one or more of the plurality of anti-rotation elements has the form of a discontinuous indentation, discontinuous recess and/or discontinuous groove.

4. The ceramic femoral resurfacing head prosthesis as claimed in claim 1, wherein the at least two-part angular transition includes a first curved part having a radius in a range of 5 mm to 150 mm, a second curved part having a radius in a range of 10 mm to 100 mm, and a third curved part having a radius in a range of 0.5 mm to 2 mm.

5. The ceramic femoral resurfacing head prosthesis as claimed in claim 4, wherein the first and second curved parts and the second and third curved parts are contiguous with each other.

6. The ceramic femoral resurfacing head prosthesis as claimed in claim 1, wherein the at least two-part angular transition includes at least one flat in a longitudinal direction of the stem.

7. The ceramic femoral resurfacing head prosthesis as claimed in claim 1, wherein the at least two-part angular transition is or includes a catenary curve.

8. The ceramic femoral resurfacing head prosthesis as claimed in claim 1, wherein the inner fixation surface includes a skirt between the inner-land portion and the rim.

9. The ceramic femoral resurfacing head prosthesis as claimed in claim 8, wherein the inner fixation surface includes at least one circumferentially elongate recess at the skirt to prevent or inhibit pull-off removal of the head prosthesis.

10. The ceramic femoral surfacing head prosthesis as claimed in claim 9, wherein the circumferentially elongate recess is an endless channel.

11. The ceramic femoral surfacing head prosthesis as claimed in claim 8 wherein the skirt is preferably cylindrical or substantially cylindrical, or frusto-conical or substantially frusto-conical.

12. The ceramic femoral resurfacing head prosthesis as claimed in claim 1, wherein the rim of the ceramic femoral resurfacing head prosthesis defines an asymmetrical profile between the inner fixation surface and the outer contact surface with two or more different arcs having a radius in a range of 0.2 mm to 1.5 mm.

* * * * *